US006764441B2

(12) United States Patent
Chiel et al.

(10) Patent No.: US 6,764,441 B2
(45) Date of Patent: Jul. 20, 2004

(54) PERISTALTICALLY SELF-PROPELLED ENDOSCOPIC DEVICE

(75) Inventors: Hillel J. Chiel, University Heights, OH (US); Roger D. Quinn, Akron, OH (US); Randall D. Beer, South Euclid, OH (US); Elizabeth D. Mangan, Dublin, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 10/140,371

(22) Filed: May 8, 2002

(65) Prior Publication Data

US 2003/0065250 A1 Apr. 3, 2003

Related U.S. Application Data

(60) Provisional application No. 60/322,464, filed on Sep. 17, 2001.

(51) Int. Cl.$^7$ ................................. A61B 1/04
(52) U.S. Cl. ..................... 600/115; 600/116; 600/151; 604/95.03
(58) Field of Search ............................ 600/115, 116, 600/156, 114, 151, 146, 152, 101, 159; 604/95.01, 95.03, 95.05; 73/865.8, 866.5

(56) References Cited

U.S. PATENT DOCUMENTS

| | | | |
|---|---|---|---|
| 4,176,662 A | * 12/1979 | Frazer | 600/114 |
| 4,281,646 A | * 8/1981 | Kinoshita | 600/157 |
| 4,690,131 A | * 9/1987 | Lyddy et al. | 600/115 |
| 5,090,259 A | 2/1992 | Shishido et al. | |
| 5,144,848 A | * 9/1992 | Uenishi et al. | 73/866.5 |
| 5,662,587 A | 9/1997 | Grundfest et al. | |
| 5,810,717 A | * 9/1998 | Maeda et al. | 600/151 |
| 6,007,482 A | * 12/1999 | Madni et al. | 600/115 |

OTHER PUBLICATIONS

Cheryl Ajluni, "Microsensors Move Into Biomedical Applications," Electronic Designs, vol. 44, No. 11, pp. May 28, 1996.

Matthew C. Birch et al., "Design of a Cricket Microrobot," Proc. IEEE Int'l Conference on Robotics and Automation, vol. 2, 1109–1114, Apr. 2000.

Koji Ikuta et al., "Portable Virtual Endoscope System with Force and Visual Display for Insertion Training," Lecture Notes in Computer Science, vol. 1935, pp. 907–920, 2000.

William M. Kier et al., "Tongues, Tentacles and Trunks: The biomechanics of Movement in Muscular Hydrostats," Zoological J. of Linnean Soc., vol. 83, No. 4, pp. 307–324, 1985.

Sanjiv Kumar et al., "Design of a vision–guided microrobotic colonoscopy system," Advanced Robotics, vol. 14, No. 2, pp. 87–104, 2000.

Kim I. Quillin, "Ontogenetic Scaling of Burrowing Forces in the Earthwork *Lumbricus Terrestris*," J. Experimental Biology, vol. 203, No. 18, 2757–2770, Sep. 2000.

Michael S. Triantafyllou et al., "An Efficient Swimming Machine," Scientific American, vol. 272, No. 3, pp. 64–70, Mar. 1995.

Vijayan K. Asari, et al., "A Fully Autonomous Micororobotic Endoscopy System," J. of Intelligent & Robotic Systems, 28:325–341, 2000.

(List continued on next page.)

Primary Examiner—John P. Leubecker
(74) Attorney, Agent, or Firm—Banner & Witcoff, Ltd.

(57) ABSTRACT

Expandable actuators surround a central conduit. Each actuator comprises a bladder that, when fluid is introduced, expands laterally while contracting longitudinally. A restorative spring can be placed inside a bladder and between the two ends to restore the actuator to its original shape as fluid is withdrawn. Multiple actuators can be placed in series to successively inflate and deflate and generate a peristaltic motion. One or more Shape Memory Alloy (SMA) springs can be affixed to one or more restorative springs to cause bending motion.

60 Claims, 17 Drawing Sheets

OTHER PUBLICATIONS

Randall D. Beer, "On the Dynamics of Small Continuous–Time Recurrent Neural Networks," Adaptive Behavior, vol. 3, No. 4 469–509, 1995.

Randall D. Beer et al., "Biorobotic approaches to the study of motor systems," Current Opinion in Neurobiology, vol. 8, pp. 777–782, 1998.

Randall D. Beer et al., "Evolution and Analysis of Model CPGs for Walking: II. General Principles and Individual Variability," J. of Computational Neuroscience, 7:119–147, 1999.

Garth Chapman, "Of the Movement of Worms," J. Experimental Biology, vol. 27, pp. 29–39, 1950.

Hillel J. Chiel et al., "Evolution and Analysis of Model CPGs for Walking: I. Dynamical Modules," J. of Computational Neuroscience, 7:99–118, 1999.

Hillel J. Chiel et al., "Biomechanics of a muscular hydrostat: a model of lapping by a reptilian tongue," Biological Cybernetics, vol. 67, 403–415, 1992.

Ching–Ping Chou et al., "Measurement and Modeling of McKibben Pneumatic Artificial Muscles," IEEE Transactions on Robotics and Automation, vol. 12, pp. 90–102, 1996.

Paolo Dario et al., "Development and In Vitro Testing of a Miniature Robotic System for Computer Assisted Colonscopy," Computer Aided Surgery, 4:1–14 (1999).

Paolo Dario et al., "Micro–systems in biomedical applications," J. Micromechanics and Microengineering, vol. 10, pp. 235–244 (2000).

Kenneth S. Espenschied et al., "Biologically based distributed control and local reflexes improve rough terrain locomotion in a hexapod robot," Robotics and Autonomous Systems, vol. 18, pp. 59–64, (1996).

Robert J. Full, Integration of Individual Leg Dynamics with Whole Body Movement in Arthropod Locomotion, Biol. Neural Networks in Invertebrate Neuroethology and Robotics, Chap. 1, pp. 3–20, 1993.

Ken–Ichi Funahashi et al., "Approximation of Dynamical Systems by Continuous Time Recurrent Neural Networks," Neural Networks, vol. 6, No. 5, pp. 801–806 (1993).

H.D. Hoeg et al., "Biomechanical Modeling of the Small Intestine as Required for the Design and Operation of a Robotic Endoscope," pp. 1–8 (2000).

Gabriel Idden et al., "Wireless capsule endoscopy," Nature vol. 405, p. 417 (2000).

Koji Ikuta et al., "Mathematical Model and Experimental Verification of Shape Memory Alloy for Designing Micro Actuator," Micro Electric Mechanical Systems, pp. 103–108 (1991).

Joseph B. Keller, "Crawling of Worms," J. Theoretical Biology, vol. 104, pp. 417–422 (1983).

Glenn K. Klute et al., "McKibben Artificial Muscles: Pneumatic Actuators with Biomechanical Intelligence," IEEE/ASME, pp. 221–226 (1999).

Glenn K. Klute et al., "Accounting for Elastic Energy Storage in McKibben Artificial Muscle Actuator," ASME J. Dynamic Systems, Measurement & Control, 122(2):386–388 (Jun. 2000).

John Muir Kumph, "A Fast–Starting and Maneuvering Vehicle, the ROBOPIKE," Int'l Symp on Seawater Drag Reduction, pp. 485–490 (1998).

John E. Lewis et al., "Representation of Touch Location by a Population of Leech Sensory Neurons," J. of Neurophysiology, vol. 80, pp. 2584–2592 (1998).

G.M. Nelson et al., "Design and Simulation of a Cockroach–Like Hexapod Robot," IEEE Int'l Conf. On Robotics and Automation, 1106–1111 (1997).

Kim I. Quillin, "Kinematic Scaling of Locomotion by Hydrostatic Animals: Ontogeny of Peristaltic Crawling by the Earthworm *Lumbricus Terrestris*," J. Experimental Biology, vol. 202, pp. 661–674 (1999).

Kim I. Quillin, Ontogenetic Scaling of Hydrostatic Skeletons: Geometric, Static Stress and Dynamic Stress Scaling of the Earthworm *Lumbricus Terrestris*, J. Expermental Biology, vol. 201, pp. 1871–1883 (1998).

Brian K. Shaw, "Relative Roles of the S Cell Network and Parallel Interneuronal Pathways in the Whole–Body Shortening Reflex of the Medicinal Leech," J. Neurophysiology, vol. 82, pp. 114–1123 (1999).

M.V.K. Sukhdeo et al. "Behavioural adaptation of the tapeworm, *Hymenolepis diminuta* to its environment," Parasitology, vol. 104, pp. 331–336 (1992).

Bertrand Tondu et al., "McKibben Artificial Muscle Robot Actuators," IEEE Control Systems, vol. 20, pp. 15–38 (2000).

Ravi Vaidanathan et al., "A hydrostatic robot for marine applications," Robotics and Autonomous Systems, vol. 30, pp. 103–113 (2000).

Sung–Nien Yu et al., "A nonisometric kinetic model for smooth muscle," Am. J. Physiology, vol. 41, pp. C1025–C1039 (1997).

* cited by examiner

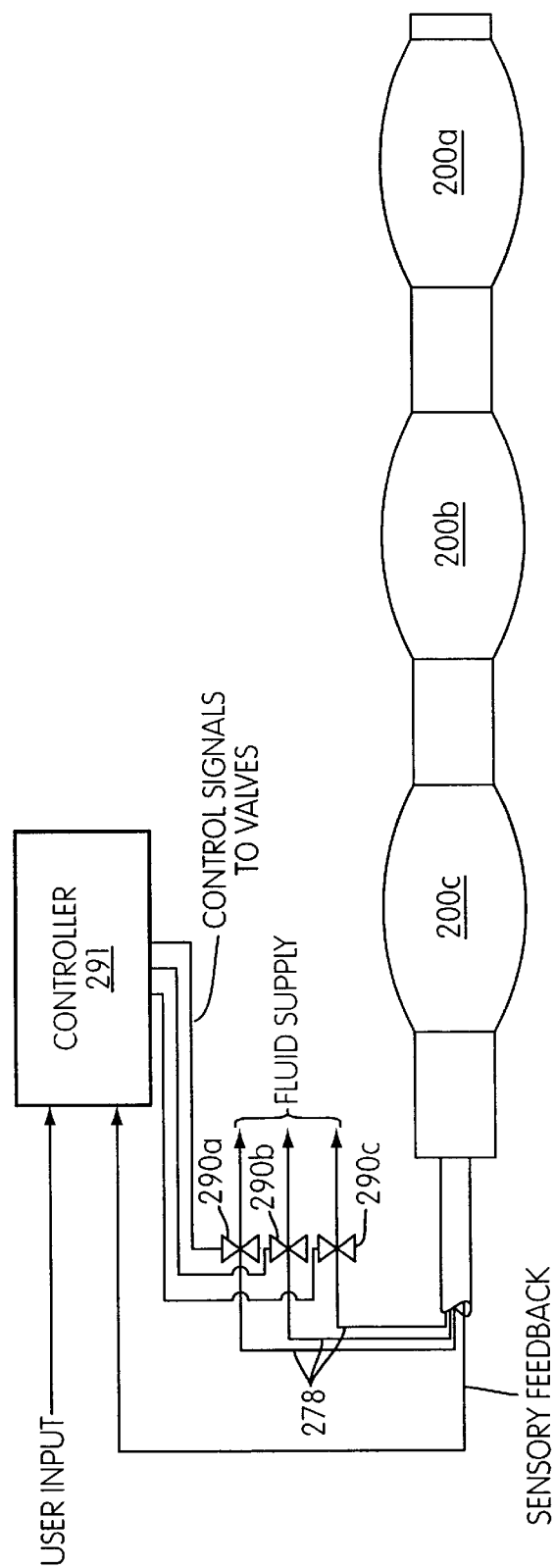

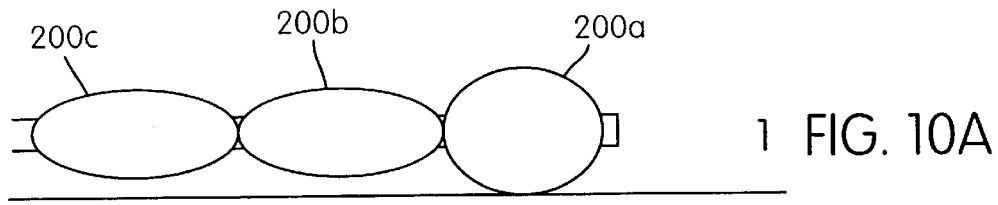
1 FIG. 10A
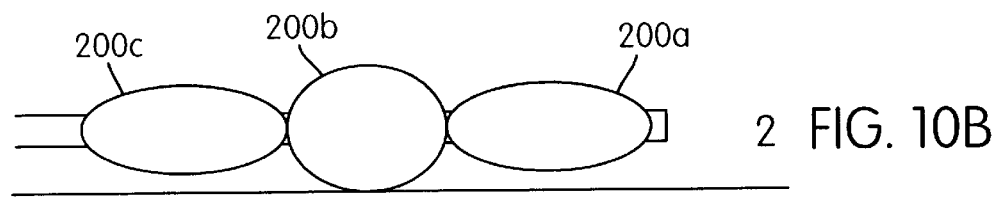
2 FIG. 10B
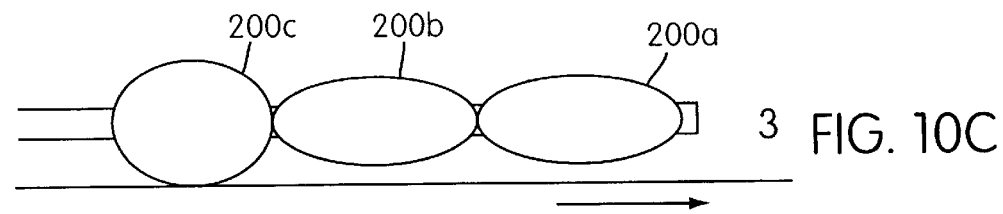
3 FIG. 10C
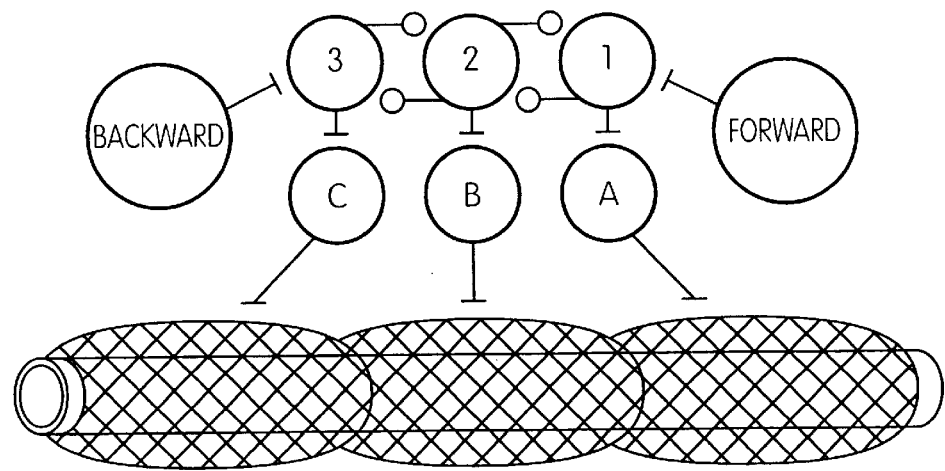
FIG. 10D

PERISTALTICALLY SELF-PROPELLED ENDOSCOPIC DEVICE

CROSS-REFERENCE TO RELATED APPLICATIONS

This application claims the benefit of U.S. Provisional Application Ser. No. 60/322,464, filed Sep. 17, 2001, hereby incorporated herein by reference.

BACKGROUND OF THE INVENTION

In the last two decades, minimally invasive surgery (MIS) has reduced the trauma of surgery, speeded recovery times, and significantly reduced the cost of many surgical procedures. MIS has been greatly advanced by the growing miniaturization of medical technology. Using small incisions, and by introducing endoscopes or catheters with miniaturized sensors and tools at their tips, it is often possible to visualize, diagnose, and correct medical conditions that previously required major surgical intervention. A major obstacle to further advances in minimally invasive surgery, however, is the need to push catheters and endoscopes into the tortuous vessels, passageways and cavities of the body. Pushing a flexible instrument such as an endoscope risks buckling and damage to the device. More important, however, pushing an endoscope or catheter into the body risks perforating or otherwise damaging tissue, and can be extremely uncomfortable for the patient. For example, there is currently a controversy over use of sigmoidoscopy or colonoscopy to routinely to monitor and prevent colon cancer. Although colonoscopy provides a physician with a superior view of the entire colon, it is an invasive and difficult procedure requiring the colonoscope to be pushed around the right angle bends in the colon, and it requires anesthesia to reduce patient discomfort. Endoscopes and catheters could be further improved if they could pull themselves forward, rather than having to be pushed into position, and if they could bend regionally along their length as well as at their tips. Such devices could be further enhanced if they could sense local conditions and reflexively alter the propulsive force and/or direction.

It has been suggested to implement an autonomous catheter using localized vacuum and a bellows-like expansion and contraction to move itself through tubes and excised segments of porcine intestine. See Asari, V. K., S. Kumar, and I. Kassim, A fully autonomous microrobotic endoscopy system. J Intel Robot Sys, 2000. 28: p. 325–341. As understood, however, the center of this device may not be hollow.

Furthermore, studies of this device indicate that the vacuum clamp used to anchor the device before its center is extended by a bellows may be somewhat ineffective in dealing with changing colon diameters. Other known devices include a disposable ingestible capsule that can provide physicians with images of the gastro-intestinal tract and location information. A brief description of this device was published by Iddan, G., Meron, G., Glukhovsky, A., and Swain, P. in "Wireless capsule endoscopy," Nature 405:417, 2000. Because this device is moved entirely through the peristaltic action of the patient's gastrointestinal system, however, it does not allow a physician to direct it or move it backwards.

Hence, there remains a need for a self-propelled device (i.e., not needing to be to be pushed) that provides a physician full control over the position of an endoscope or catheter. It would also be advantageous if such a device had certain reflexive capabilities that allowed a physician to utilize the device with greater ease. For example, if an endoscope could make reflexive adjustments in force, it would greatly facilitate a physician's ability to guide and oversee effective surgeries and other procedures.

Endoscopes, catheters, and miniaturized tools with these capabilities could offer a wide variety of useful applications. A device could pull itself into the coronary arteries, and then scrape and suction away atherosclerotic plaque, stopping if it encountered a vessel wall. Another device of similar design could pull itself through the colon, and scrape and suction away precancerous polyps. Another device with these capabilities could pull itself into an artery of the brain, and scrape and suction away a clot. Moreover, such devices could have countless non-medical applications. For example, maintenance of traps and other complex plumbing in domestic and industrial settings currently relies either on pushing a passive device through an obstruction (e.g., a plumber's snake) or chemically dissolving an obstruction. A self-propelled device able to negotiate intricate bends and other pathways could actively move towards an obstruction and apply small amounts of chemical to dissolve the obstruction, suck out material, or (if equipped with an appropriate manipulator) actively remove the material in the obstruction. Countless other possibilities exist.

Mechanical principles helpful in achieving these ends can be observed in hydrostatic animals such as worms or leeches. These organisms can insinuate themselves into highly curved and tortuous spaces. For example, the flatworm Schistosoma can successfully locomote into and anchor itself within human blood vessels. The tapeworm can locomote through and anchor itself within the human intestine. To date, however, there have only been limited attempts to adapt certain mechanical characteristics of these types of organisms to a self-propelled endoscope, catheter or similar device.

U.S. Pat. No. 5,662,587 discloses a robot that can propel itself through a body cavity by a combination of "traction" and "extension." A module enlarges by inflating a balloon or extending gripping arms, and another module either contracts or extends so as to pull (or push) the device along. In one arrangement, the '587 patent also discloses concentric bellows in the same module. However, the '587 patent still requires separate (and often complicated) mechanisms for performing the traction and extension functions. Thus, a need remains for a less intricate self-propelled robotic endoscope.

Accordingly, it is an object of this invention to provide a less complicated self-propelled device that can pull itself through tight passageways, such as may be found in the human body, without causing damage to surrounding tissue or structures. It is a further object of the invention to provide reflexive capabilities and control in such a device. Additional objects of the invention are described herein or will be apparent to those skilled in the art.

SUMMARY OF THE INVENTION

The invention comprises a self-propelled device capable of peristaltic locomotion, as well as other modes of locomotion. Peristaltic locomotion is caused by one or more actuators that surround a central flexible tube or other conduit. The device is thus able to move itself through a lumen, cavity or other area that might otherwise be inaccessible, and at the same time provide a conduit by which electrical control lines, fiber optic cables, fluid delivery tubes or other components can be extended into the region to which the device has moved itself.

In one embodiment, an actuator comprises an expandable bladder that surrounds a longitudinal section of the central tube and is fluid-impermeable at either end of that section. At least one end of the bladder is able to move toward the other end of the bladder along the central tube. Surrounding the bladder is a mesh of substantially inextensible fibers. As fluid is introduced into the region between the bladder's inner wall and the central tube's outer wall, the bladder expands. The mesh maintains the surface area of the bladder substantially constant, thereby causing at least one of the bladder's ends to move towards the other end as the bladder expands outward radially from the central tube's longitudinal axis. In this manner, a device according to the invention is able to expand laterally and contract longitudinally using a minimum number of moving parts. A restorative spring can be placed inside the bladder and between the two ends to restore the actuator to its original shape as fluid is withdrawn from the bladder. Multiple actuators can be placed in series to successively inflate and deflate. Through such successive inflation and deflation, a peristaltic motion results.

The actuator can also have one or more Shape Memory Alloy (SMA) springs affixed to the restorative spring. As an electric current is applied to the SMA spring, it contracts. The actuator thereby bends along the side of the SMA spring. The actuators can also be equipped with sensors to provide feedback for control purposes, as well as for therapeutic and diagnostic purposes.

BRIEF DESCRIPTION OF THE DRAWINGS

FIG. 9 is a schematic diagram of a control system for peristaltic motion by three actuators in series.

FIGS. 10A–10C show another mode of peristaltic motion.

FIG. 10D is a diagram of a neural network controller for the motion of FIGS. 10A–10C.

DETAILED DESCRIPTION OF THE INVENTION

The invention is described with reference to the included drawings, where like-numbered features correspond to like-numbered features in the written description. For convenience, the description refers to the invention as an endoscope, but persons skilled in the art will appreciate that the description, and hence the invention, likewise applies to catheters, colonoscopes, sigmoidascopes, and any other medical or non-medical device that must navigate through a passage, lumen, cavity or other region that is otherwise inaccessible or difficult to access.

Figure 1A:
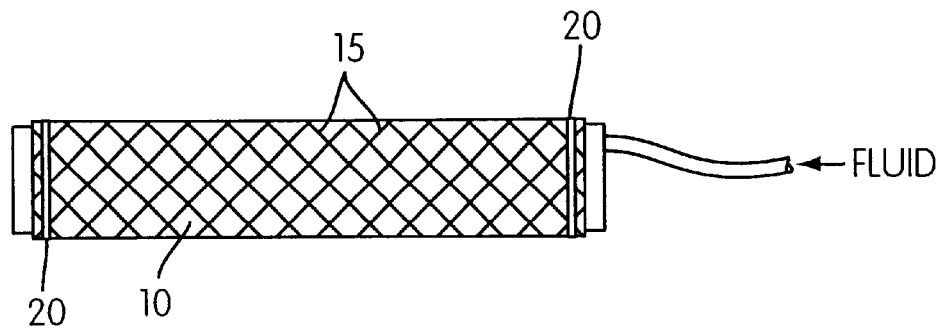
FIGS. 1A–1B are respective side views of an unexpanded and expanded existing art hydrostatic actuator.
Figure 1B:
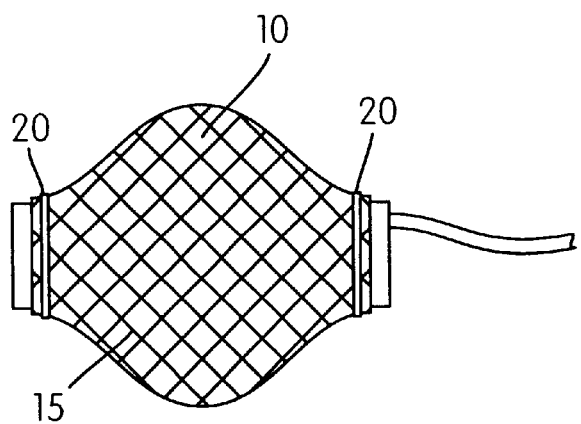

Braided pneumatic actuators, also known as McKibben artificial muscles, are mechanical actuators that mimic the action of muscles. As shown in FIG. 1A, these actuators consist of an expandable bladder 10 located inside a tubular mesh 15 made of relatively inextensible fibers. The mesh is clamped or otherwise affixed to the bladder at its ends 20. As air, water or other fluid is forced into the bladder, its volume expands. Because the inextensible fiber mesh tends to keep the surface area of the expanding bladder constant, the bladder's diameter increases while its length decreases (i.e., tending from a cylindrical toward a more spherical shape), as shown in FIG. 1B. Large versions of these actuators are commercially available, but they lack a hollow central channel.

Figure 2A:
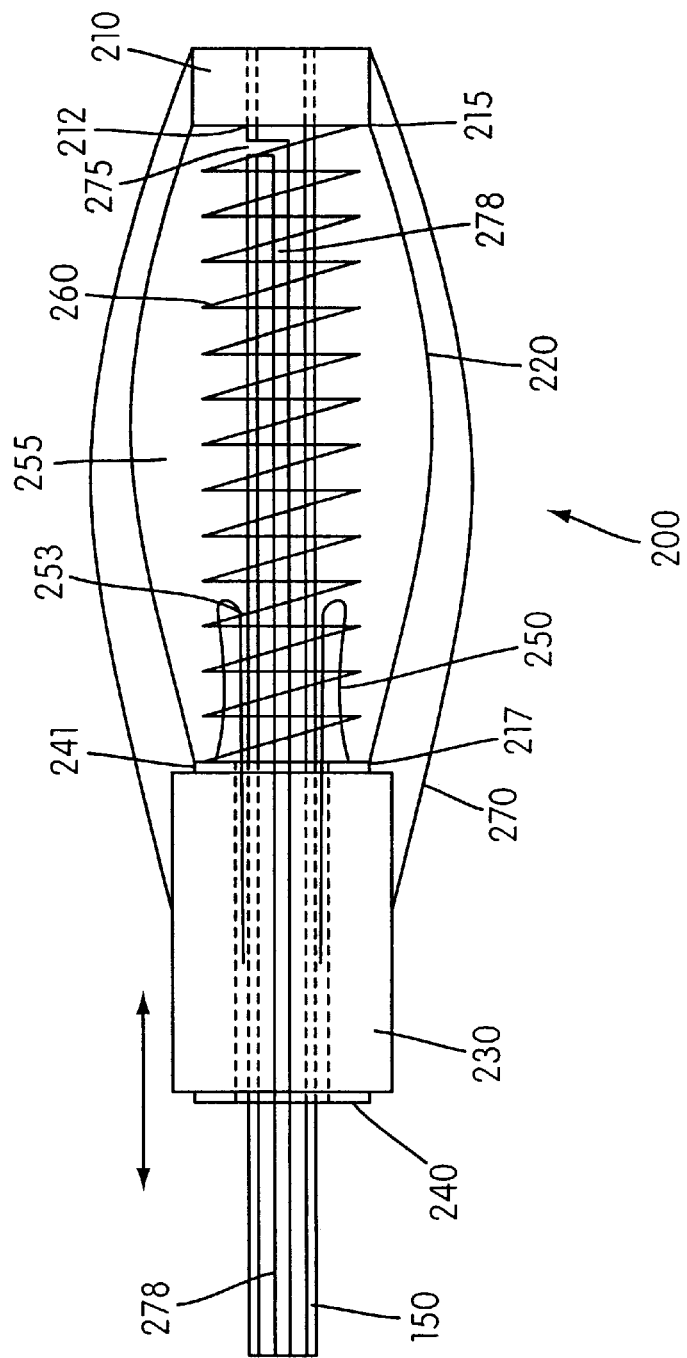
FIGS. 2A–2B are partially sectional, partially schematic side views of two embodiments of a novel actuator of the invention.
Figure 2B:
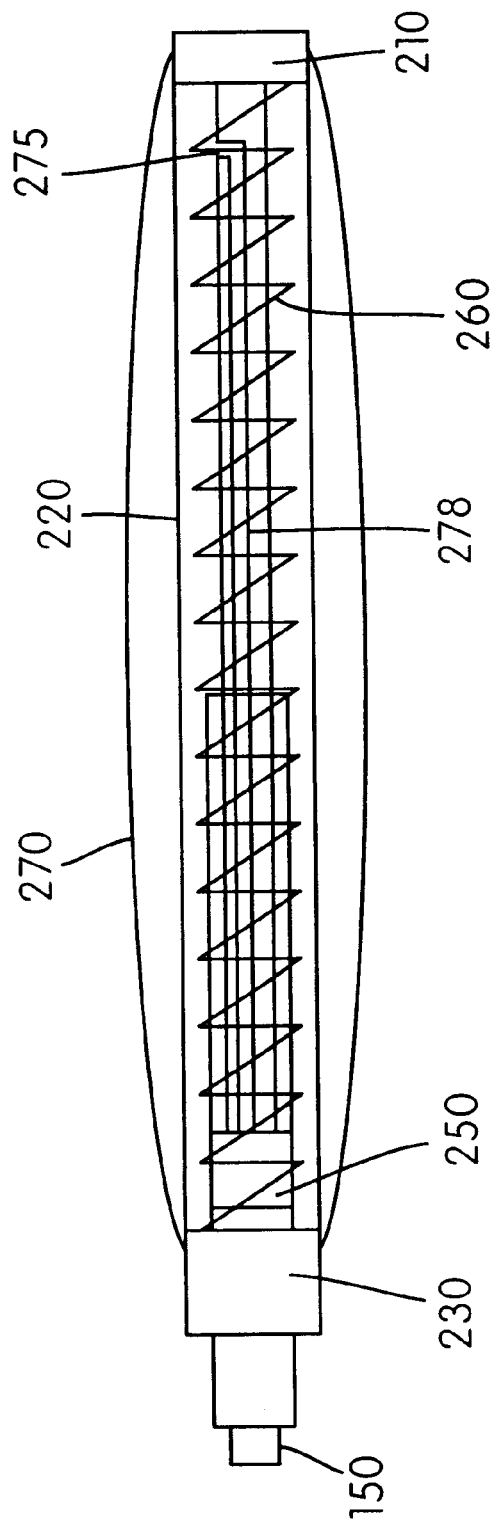
Figure 3A:
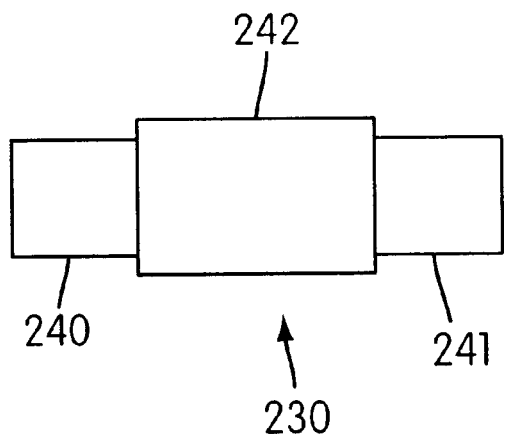
FIGS. 3A–3B are side and sectional views, respectively, of a bearing assembly of a novel actuator of the invention.
Figure 3B:
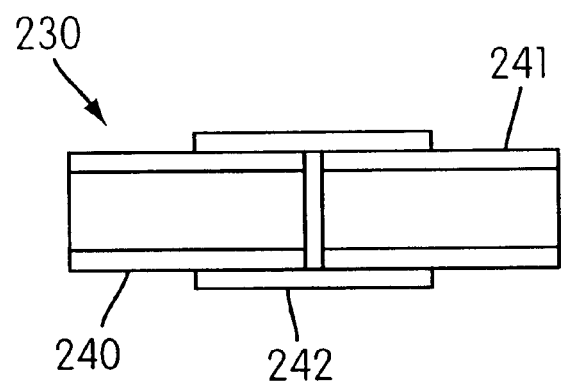

FIG. 2A shows an actuator segment 200 of the invention that employs mechanical principles similar to those of the actuator of FIGS. 1A and 1B. Actuator segment 200 is disposed upon a central tube 150 that extends the length of the actuator segment. Fixed at one end of central tube 150 is a fixed end cap 210. The interior interface 212 between tube 150 and end cap 210 is substantially fluid-impermeable. Also attached to end cap 210 is an expandable, fluid-impermeable bladder 220. Bladder 220 is sealed to end cap 210 around its periphery 215 at one longitudinal end. Also disposed on central tube 150 opposite to end cap 210 is bearing assembly 230. Bearing assembly 230 completely surrounds the outer circumference of central tube 150, and is slidable along central tube 150 for at least a portion of its length. Bearing assembly 230 comprises bearing material 240, 241. As shown in FIG. 3, bearing assembly 230 can be constructed from two thermoplastic bearings 240, 241 in series with one another, with a third bearing 242 placed over the two smaller bearings and glued in place or otherwise sealably attached to bearings 240 and 241. Bladder 220 is sealed at its other longitudinal end to bearing assembly 230 at substantially fluid-impermeable interface 217. Moreover, bladder 220 completely surrounds the portion of central tube 150 between end cap 210 and bearing assembly 230. A slightly modified embodiment is shown in FIG. 2B, in which the bladder 220 and mesh 270 (described below) are both attached to the third bearing 242.

Bearing assembly 230 further comprises a seal 250 disposed radially inward from interface 217. Seal 250 conforms to the outer surface of central tube 150 at interface 253. Interface 253 is substantially (although not necessarily completely) fluid-impermeable. In one embodiment, seal 250 comprises latex or similar material, and is glued or otherwise sealably fixed to the outer surface of central tube 150 at interface 253. As bearing assembly 230 moves toward end cap 210 (as described more fully below), seal 250 rides up and over itself. In other embodiments, seal 250 is not fixed to the outer wall of central tube 150, but instead provides a seal while simultaneously allowing bearing assembly 230 to move axially along central tube 150.

Bearing assembly 230, bladder 220 and end cap 210 form an expandable annular region 255. Also disposed within expandable region 255 is restorative spring 260 that biases bearing assembly 230 away from end cap 210. Surrounding bladder 220 is braided mesh 270. Mesh 270 comprises braided inextensible fiber. Mesh 270 completely surrounds bladder 220, and is attached to end cap 210 and bearing assembly 230. For purposes of illustration, more space is shown between bladder 220 and mesh 270 than would actually be present. During operation of the actuator 200, the outer surface of bladder 220 would be in contact with the inner surface of mesh 270.

Fluid port 275 is located on the central tube 150 between end cap 210 and bearing assembly 230, and allows fluid to flow from a supply tube 278 or other type of channel or conduit (not shown) within central tube 150 into and out of annular region 255. Port 275 may also be configured with one or more valves to regulate the flow of fluid, or such a valve may be located further upstream in (or upstream of) supply tube 278.

Figure 4:
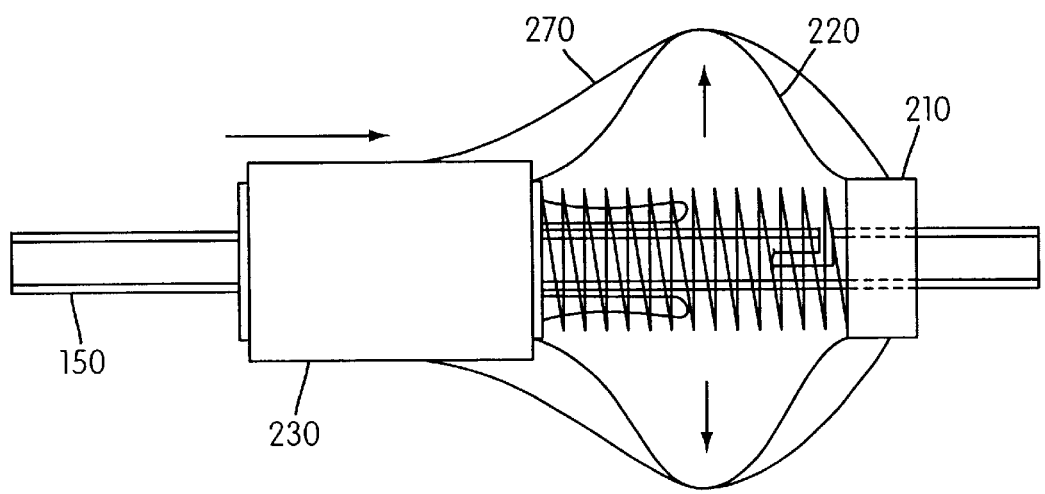
FIG. 4 is a partially sectional, partially schematic side view of a novel actuator of the invention when actuated.

The operation of actuator segment 200 is shown diagrammatically in FIG. 4, with certain details omitted for clarity. Fluid is pumped through supply tube 278 inside central tube 150 through fluid port 275 into expandable region 255, thereby causing bladder 220 to expand radially outward from central tube 150. The fluid may be a gas, a liquid, or any other form that can be pumped into region 255. Because the surface area of bladder 220 is held substantially constant by the inextensible mesh 270, volume of expandable area 255 can only increase by expanding radially outward, while simultaneously pulling bearing assembly 230 toward end cap 210. Spring 260 compresses during this process. When fluid is later released from region 255 through port 275 (now functioning as an outlet), restorative spring 260 pushes bearing assembly 230 away from end piece 210 and restores actuator 200 to its original configuration.

Bladder 220 is formed from a material that is fluid impermeable (or substantially so) but that is also sufficiently flexible. Exemplary materials include medical grade latex. Mesh 270 is formed from inextensible fibers such as nylon. It will be appreciated, however, that it is possible, using known methods and materials, to combine mesh 270 and bladder 220 into a single article of manufacture; such modifications are within the scope of the invention. End cap 210 can be aluminum. Central tube 150 can be formed from clear polyvinyl chloride (PVC) tubing. Restorative spring 260 can be a copper-beryllium spring (or can comprise multiple springs). Other materials or combinations of materials are also within the scope of the invention. Moreover, an entire actuator or series of actuators can be covered with a membrane to, e.g., allow sterilization of the device or to make it hypoallergenic.

Multiple actuators can be combined to create a self-propelled endoscope. FIGS. 5A–5F show three actuators 200a, 200b and 200c in series along central tube 150. Small projections 205 can be located on the outer surface of the actuators at multiple locations to serve as "bristles" to enhance the ability of the device to generate forces against a substrate as it moves forward. These are roughly equivalent to setae (small bristles) on the surface of earthworms that allow them to locomote peristaltically over irregular surfaces within puddles of water. Actuator 200a is substantially similar to an actuator segment 200 such as is depicted in FIG. 2A or 2B. Actuator segments 200b and 200c are substantially similar to actuator segment 200a, except that neither of their ends is fixed to a specific location along central tube 150. Specifically, bearing assembly 230a of actuator 200a also functions as the forward end cap for actuator 200b. Similarly, rear bearing assembly 230b of actuator 200b functions as the forward end cap of actuator 200c. There may be a seal (such as seal 250 in FIG. 2A) on both sides of bearing assemblies 230a and 230b, or a seal on one side of bearing assembly 230a and a seal on one side of bearing assembly 230b, or a combination of one bearing assembly with two seals and one bearing assembly with one seal. Actuator 200c has a rear bearing assembly 230c that is substantially similar to bearing assembly 230 of FIG. 2A or FIG. 2B. Additional actuator segments can be added if necessary or desirable. In certain applications, the invention can also be practiced with fewer than three actuators. Any number of actuators can be used in series (i.e. with the end of one actuator forming the front of another, as in FIGS. 5A–5F), or actuators or groups of actuators may be dispersed along a central tube 150 with actuator-free spaces between them.

Figure 5:
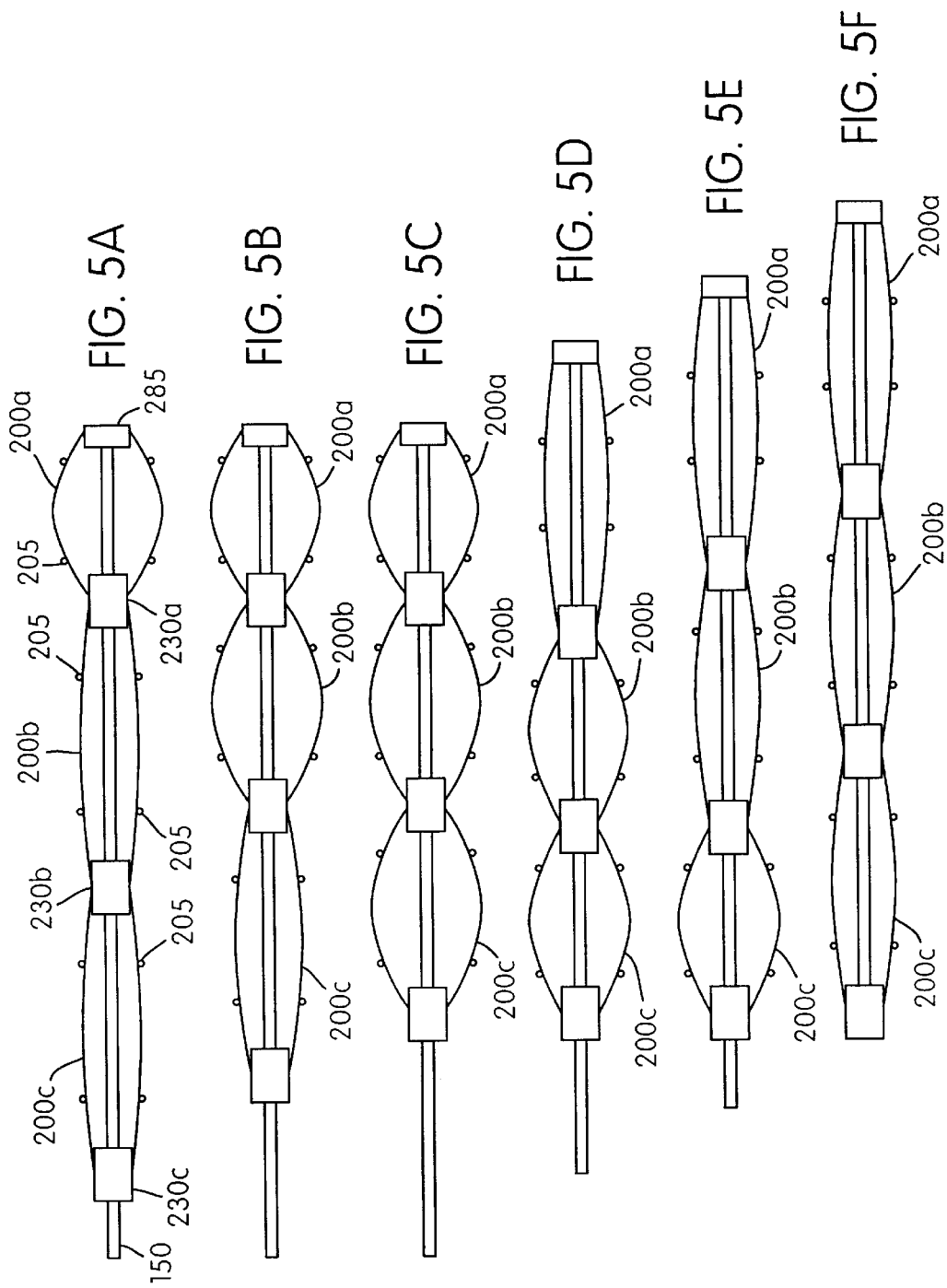
FIGS. 5A–5F are diagrams showing peristaltic motion by three actuators in series.

One mode of peristaltic movement is shown in FIGS. 5A–5F. In FIG. 5A, actuator 200a is inflated, and grips the surrounding substrate through friction and/or interaction of projections 205 with the surrounding tissue or other material. In FIG. 5B, inflated actuator 200a holds the leading end 285 in position relative to the surrounding substrate while actuator 200b inflates, and also grips the surrounding substrate through friction and/or interaction of projections 205 with the surrounding tissue or other material. As actuator 200b inflates, it pulls actuator 200c (still uninflated) forward. In FIG. 5C, actuator 200c inflates, and grips the surrounding substrate through friction and/or interaction of projections 205 with the surrounding tissue or other material. In FIG. 5D, actuator 200a deflates, and restorative spring 260a (not shown) causes leading end 285 to move forward. In FIG. 5E, actuator 200b deflates, and spring 260b (also not shown) pushes leading end 285 further forward. In FIG. 5F, actuator 200c deflates, and spring 260c (also not shown) pushes leading end 285 even further forward. The cycle then repeats. For reverse movement, the cycle reverses, or the actuator can be manually withdrawn by pulling the central tube 150.

Figure 6:
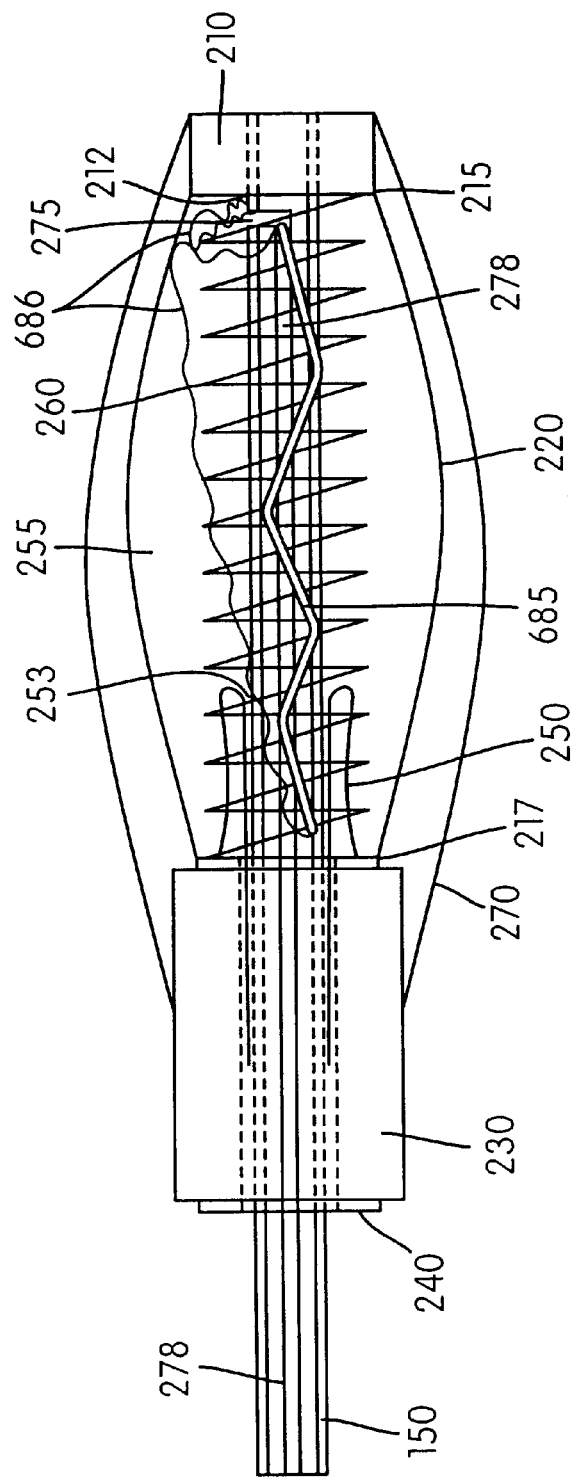
FIG. 6 is a partially sectional, partially schematic side view of another embodiment of a novel actuator of the invention.
Figure 7:
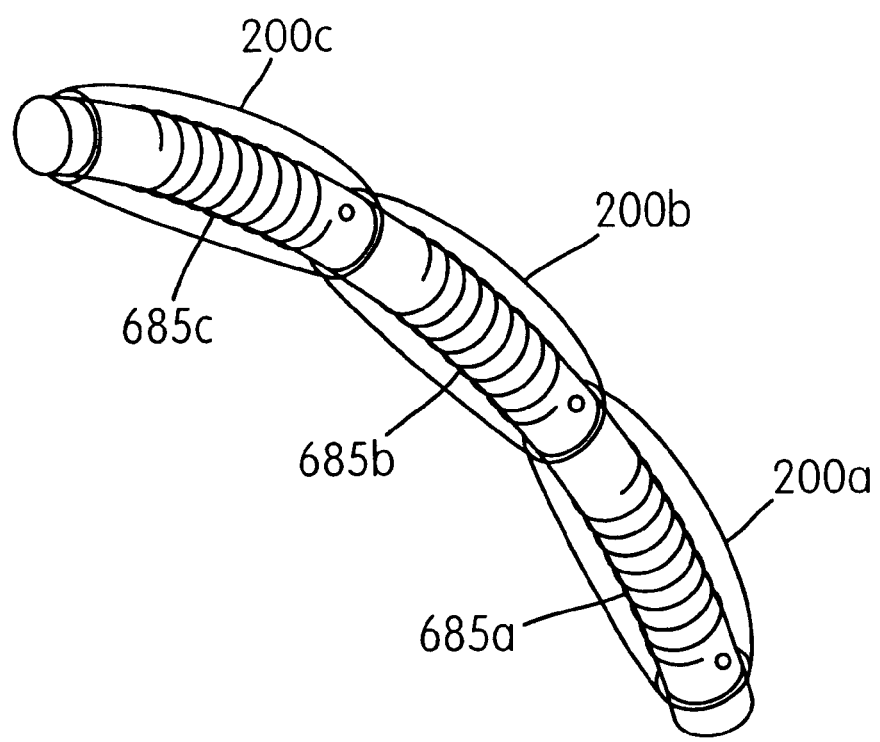
FIG. 7 is a diagram showing bending by a series of actuators of the type shown in FIG. 6.
Figure 8A:
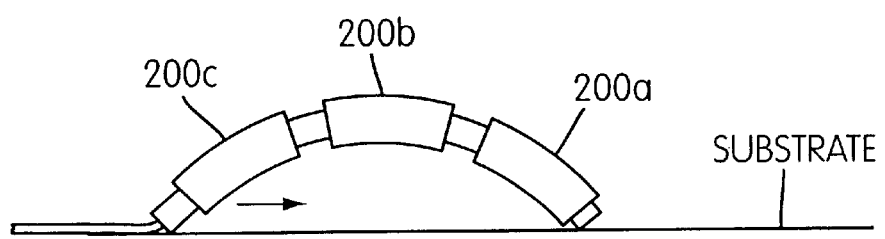
FIGS. 8A–8B show "inchworm" movement by a series of actuators of the type depicted in FIGS. 6 and 7.
Figure 8B:
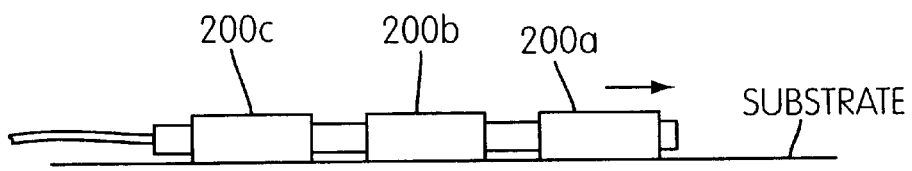

FIG. 6 shows another embodiment of an actuator that is further configured to have an autonomous bending mechanism. FIG. 6 shows an actuator substantially similar to that of FIGS. 2A and 4, where similarly numbered components have functions similar to those of FIGS. 2A and 4. However, the actuator of FIG. 6 also has one or more shape memory alloy (SMA) linear springs 685 wrapped around the front and back coils of the restorative spring 260. SMA linear springs can be placed on the top, bottom and both sides of the restorative spring 260. When activated by an electric current (fed by wires 686), SMA linear spring 685 contracts, pulling the end coils of the central spring together on the side that contracts, inducing the entire spring and central tube to bend. By placing linear SMA springs 685 on all sides of restorative spring 260, each segment of the device can bend in all three dimensions, causing the device to bend all along its length. FIG. 7 shows this bending in three successive actuators 200a, 200b and 200c. FIGS. 8A and 8B show another mode of locomotion enabled by bending, similar to that observed in an inchworm. As the front of actuator 200a grips the substrate by friction or other means, the actuators 200a, 200b and 200c bend, thus pulling actuators 200b and 200c toward actuator 200a. As the actuators straighten, actuator 200c grips the substrate, and actuators 200b and 200a are moved forward.

FIG. 9 depicts an exemplary control system for a three actuator endoscope of the present invention. Fluid lines 278 feed fluid to the bladders 220a–220c of actuators 200a–200c, respectively. Interposed between each fluid control line 278 and a pressurized fluid supply are three control valves 290a, 290b and 290c. Although not shown, multiple valves could be used on each fluid line 278, with one valve serving as fluid inlet and another valve serving as exhaust. Valves 290a–290c can be any of a variety of electrically controlled valves that are known in the art and commercially available, and are controlled by separate electrical control lines supplying control signals to valves 290a–290c. These control signals are issued by a controller 291, which may comprise a microprocessor and associated hardware and software, or any other individual or combination of devices for processing electrical signals. Controller 291 receives sensory feedback from sensors on one or more of the actuators (or otherwise located on the endoscope), which sensors are discussed more fully below. Controller 291 also receives user input, which can range from commands as simple as on/off or forward/reverse, to complex motions and instructions to respond according to various sensory inputs. Controller 291 combines these commands and/or sensory feedback inputs and issues control signals to valves 290a–290c to inflate or deflate as necessary to achieve the desired motion. Microprocessors and other electronic components necessary to construct the controller, as well as the proper combination and programming thereof, are well known in the art once specifically desired motions and desired responses are identified. Accordingly, details of the controller's construction and programming to control the actuators of the invention are not necessary.

An exemplary forward locomotion control sequence can be provided in tabular form. If each of valves 290a–290c is turned completely on for 0.6 seconds and then turned completely off for 0.4 seconds in series over a 1 second cycle (with "on" meaning fluid is fed into an actuator and "off" meaning fluid flow is stopped and fluid within the actuator allowed to exhaust), the sequence of control pulses to actuators 200a –200c is as set forth in Table 1. Reverse locomotion could be achieved by reversing order of activation, i.e., switching the first and third columns of Table 1.

TABLE 1

|  | valve 290a | valve 290b | valve 290c |
| --- | --- | --- | --- |
| 0.2 sec | on | off | off |
| 0.4 sec | on | on | off |
| 0.6 sec | on | on | on |
| 0.8 sec | off | on | on |
| 1.0 sec | off | off | on |

FIGS. 10A–10C show another mode of peristaltic motion. In particular, not all actuators are fully inflated at once. As shown in FIG. 10A, actuator 200a inflates. As actuator 200a deflates, actuator 200b inflates, leading to the configuration of FIG. 10B. As actuator 200b deflates, actuator 200c inflates, leading to the configuration of FIG. 10C. The cycle can then repeat. A control algorithm for this or other modes of movement could be generated using a variety of control architectures, including known continuous time recurrent neural networks (CTRNNs) and evolutionary algorithms.

An exemplary neural network controller for the sequence of 10A–10C is shown in FIG. 10D. The artificial neural network neurons labeled "A", "B" and "C" are "motor neurons". When activated, they actuate corresponding valves causing fluid to flow through ports 275a, 275b and 275c of the three actuator segments 200a, 200b and 200c and inflate corresponding bladders 220a, 220b and 220c. The neurons labeled "1", "2" and "3" are "interneurons", i.e., they only act via the "motor neurons". Each model neuron shown in the diagram is a continuous time recurrent neuron. If none of the motor neurons is on, the internal springs will induce each of the actuators to assume an elongated shape. The neuron labeled "Forward" excites interneuron 1, inducing motor neuron A to contract actuator 200a. At the same time, interneuron 1 inhibits interneuron 2. However, the bias and active conductance (self-connection) of interneuron 1 are set so that the excitation from the "Forward" neuron is not sufficient to keep it on permanently. As interneuron 1 begins to turn off, interneuron 2 turns on, inhibiting interneurons 1 and 3 and activating motor neuron B, so that bladder 220b of actuator 200b is inflated. Again, the active conductance of interneuron 2 is set so that it does not remain on, and then interneuron 3 is released from inhibition, activating motor neuron C and causing actuator 200c to contract. Interneuron 3 also does not remain stably on, and the excitatory drive from the "Forward" neuron re-excites interneuron 1, and the cycle repeats. Once generated, such oscillatory neural networks can be programmed into a microprocessor using techniques known in the art. Reverse peristaltic motion can be obtained by activating the neuron labeled "Backward", which induces excitation in the interneurons and motor neurons in the reverse order.

Figure 11:
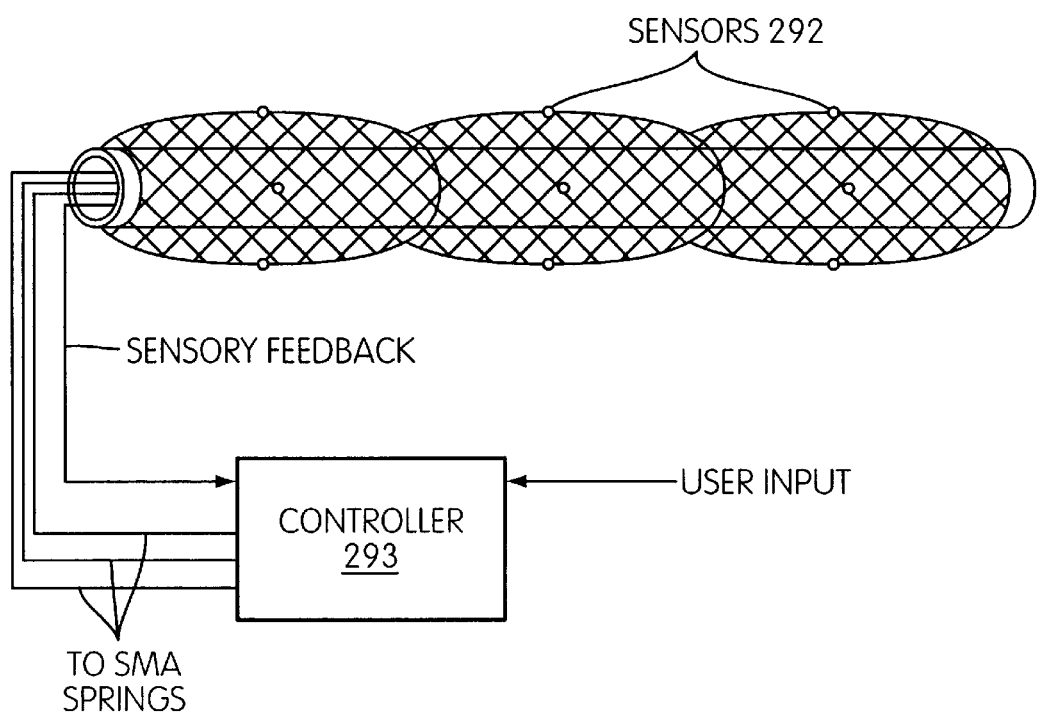
FIG. 11 is a schematic diagram of a control system for the "inchworm" mode of movement.
Figure 12:
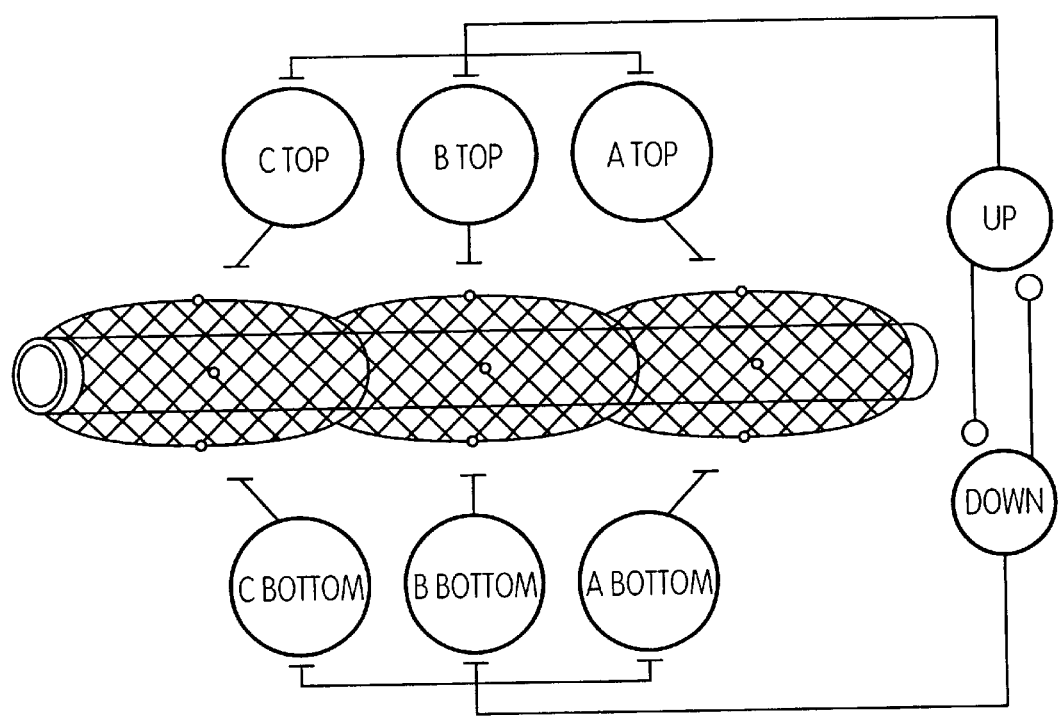
FIG. 12 is a diagram for a neural network controller for "inchworm" movement.

An exemplary controller for the SMA springs in the actuators is shown in FIG. 11. As with the controller of FIG. 9, the controller of FIG. 11 receives sensory feedback from sensors 292 on the endoscope. The controller 293 combines this feedback with user input commands to issue control signals to SMA springs in the actuators, thereby causing each actuator to bend as desired. An artificial neural network controller for inchworm locomotion is depicted in FIG. 12. When the neuron labeled "Up" is active, it inhibits the neuron labeled "Down", at the same time that it simultaneously activates the neurons labeled "A top", "B top" and "C top" which allow current to flow through the top SMA springs in each actuator, causing the entire segment to bend upwards. As the excitation in neuron "Up" diminishes, the neuron labeled "Down" escapes from inhibition, inhibits the "Up" neuron, and simultaneously activates the three neurons labeled "A bottom", "B bottom" and "C bottom" which allow current to flow through the bottom SMA springs in each actuator, causing the entire actuator to bend downwards, pushing it against the substrate and causing the device to take one inchworm step forward.

A single controller may control both actuator inflation/deflation and SMA spring actuation. Moreover, the device may be controlled by combinations of neural network control and other control algorithms. Again, once the specific movements and responses desired by the endoscope are identified, constructing and programming such a controller is a routine matter within the abilities of a person skilled in the art.

Figure 13:
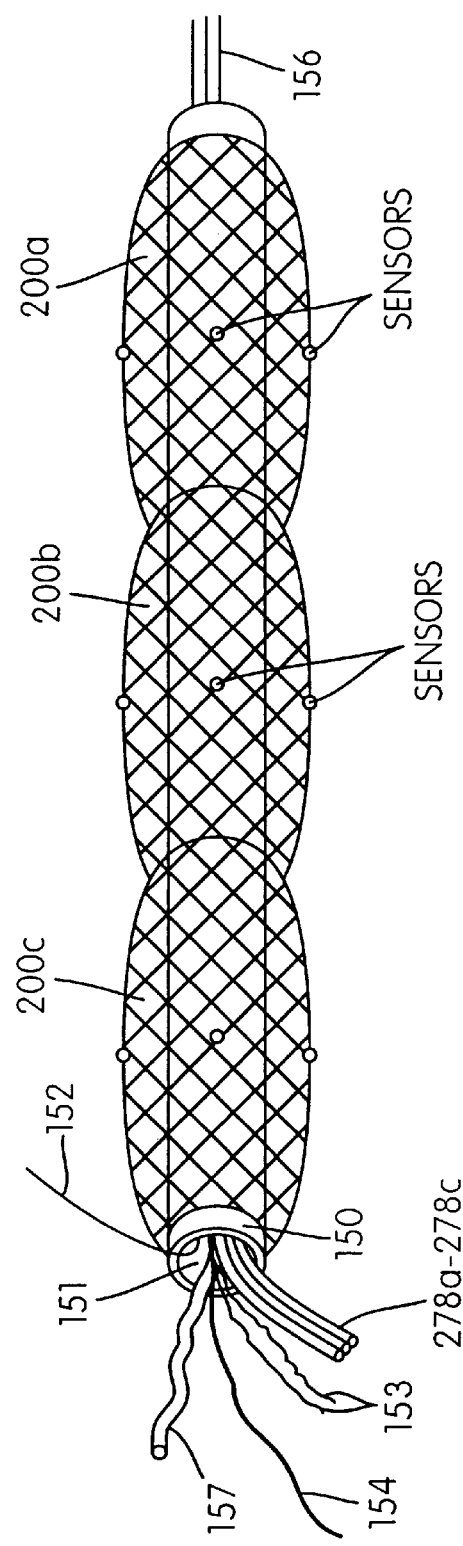
FIG. 13 shows one embodiment of an endoscope according to the invention.

Operation of the invention can be enhanced through the use of sensors disposed on the actuators or elsewhere on an endoscope of the invention. For example, sensory feedback can added obtained using hydrostatic pressure detectors. Commercially available pressure sensors, on the order of 1 mm in diameter, can be encased in silicon and attached to the outside of one or more actuators. As shown in FIG. 13, sensors can be mounted on the surface of an actuator. Although only a few such sensors are shown, any desired number could be used. Pressure sensors sensitive to the range of pressures likely to be encountered are used; for medical purposes, those pressures are likely to be below the peak of blood pressure or 300 mm mercury (0.4 bar or 5.8 p.s.i.). Sensory feedback from the pressure sensors would permit, for example, programming of reflexes similar to those observed in worms and leeches. For example, when touched on the side, leeches show a bending reflex away from that side. Similarly, when a rapid pressure increase is sensed on one side of an actuator, the shape memory alloy spring on the opposite side of the central spring can be activated, inducing that part of the actuator to bend away from the stimulus. Worms and leeches also show withdrawal reflexes that allow them to back away from obstructions. If pressure sensors indicate increased pressure on all sides of the device, this could be used to switch activation from the "Forward" neuron to the "Backward" neuron, causing the device to move peristaltically in the opposite direction, and thus allowing it to back away from an obstruction or a narrowing passageway. The device could also have steering controls that will allow a physician to override the autonomous movements of the device at any time, as well as taking control should the endoscope encounter a situation that it cannot manage automatically. For example, if there are branches in the vessel or lumen through which the device is moving, the physician will be able to bend the tip of the device in order to select the correct branch.

The invention is not limited to pressure sensors. Any sensor providing feedback based on the environment encountered by the endoscope could be used. Sensors could detect changes in temperature, chemical changes, electrical changes, light changes or any other measurable quantity.

FIG. 13 shows an exemplary endoscope of the invention. Three actuators 200a, 200b and 200c are situated on the end of the endoscope. Situated within main lumen 151 of central tube 150 are fluid conduits 278a, 278b and 278c to inflate and deflate actuators 200a, 200b and 200c, respectively. Although the invention is not limited by the type of fluid employed, this fluid could be an isotonic sterile saline solution. Optionally, a safety cable 152 may also be included within main lumen 151 to facilitate withdrawal of the device by pulling on the cable. Also contained within main lumen could be one or more cables 153 to carry electronic signals from (or to) sensors on the outside surface of the endoscope. These sensors can be configured to provide sensory feedback for purposes of guiding the endoscope (as set forth above), or can be configured for diagnostic (e.g., ultrasound) or therapeutic purposes. One or more optical fibers 154 may also be employed to allow fiber optic viewing, or to facilitate the use of lasers for surgery or other procedures. One or more microneedles 156 may also be placed on the endoscope to facilitate precise delivery of drugs or other agents, with supply tubes 157 for such needles also fitting within central lumen 151. It will also be appreciated that any of fluid conduits 278a–278c, safety cable 152, electronic cables 153 or other components may be incorporated into the wall of central tube 150 to leave central lumen 150 clear for less obstructed passage of other components.

Although the predictive value will vary depending upon the physical dimensions and materials used for the invention, it is possible to mathematically model the dynamics and kinematics of the novel actuator based on published literature regarding prior art McKibben artificial muscles. Such literature has parameterized the properties of McKibben artificial muscles using three parameters: the initial braid angle $\alpha_0$, the initial muscle length $l_0$, and the initial muscle radius, $r_0$, which is the initial radius of the rubber inner tube assumed in contact with the braided shell. One can solve for the length (l) and the radius (r) during inflation by realizing that $l/l_0 = \cos(\alpha)/\cos(\alpha_0)$, and that $r/r_0 = \sin(\alpha)/\sin(\alpha_0)$, so that:

$$r = r_0 \frac{\sqrt{1 - \cos(\alpha_0)^2 (l/l_0)^2}}{\sin(\alpha_0)} \quad (1)$$

Using the principle of virtual work, $\delta W_{lateral\ pressure} + \delta W_{axial\ pressure} + \delta W_{equilibrium\ force} = 0$, which implies that $(2\pi rlP)(+\delta r) - (\pi r2P)(-\delta l) - F(-\delta l) = 0$. Using this equation and equation (1) as well as the appropriate derivatives, the static forces in a McKibben artificial muscle as a function of the contraction ratio $\epsilon$ and the pressure P are given by the equation $$F_{static}(\epsilon, P) = (\pi r_0^2) P(a(1-\epsilon^2) - b) \quad (2)$$

where $a = 3/(\tan(\alpha_0))^2$, and $b = 1/(\sin(\alpha_0))^2$, and the contraction ratio $\epsilon = (l_0 - l)/l_0$ varies from 0 to a maximum contraction state ($\epsilon_{max}$) at which the force is zero. Because a McKibben artificial muscle takes on a conical shape at its ends as it contracts, thus decreasing its active part, this model is corrected by a factor k which in turn depends on pressure according to the equation $$k = a_k e^{-P} + b_k \quad (3)$$

where $a_k$ and $b_k$ are empirically determined constants. The static force model then becomes $$F_{static}(\epsilon, P) = (\pi r_0^2) P(a(1 - k\epsilon^2) - b) \quad (4)$$

Assuming that the restorative spring is a simple linear spring, the restoring force that it can generate will be characterized by the equation $$F_{spring}(\epsilon) = -k_{spring}(l - l_0) = k_{spring} l_0 \epsilon \quad (5)$$

where $k_{spring}$ is the spring constant.

Figure 14:
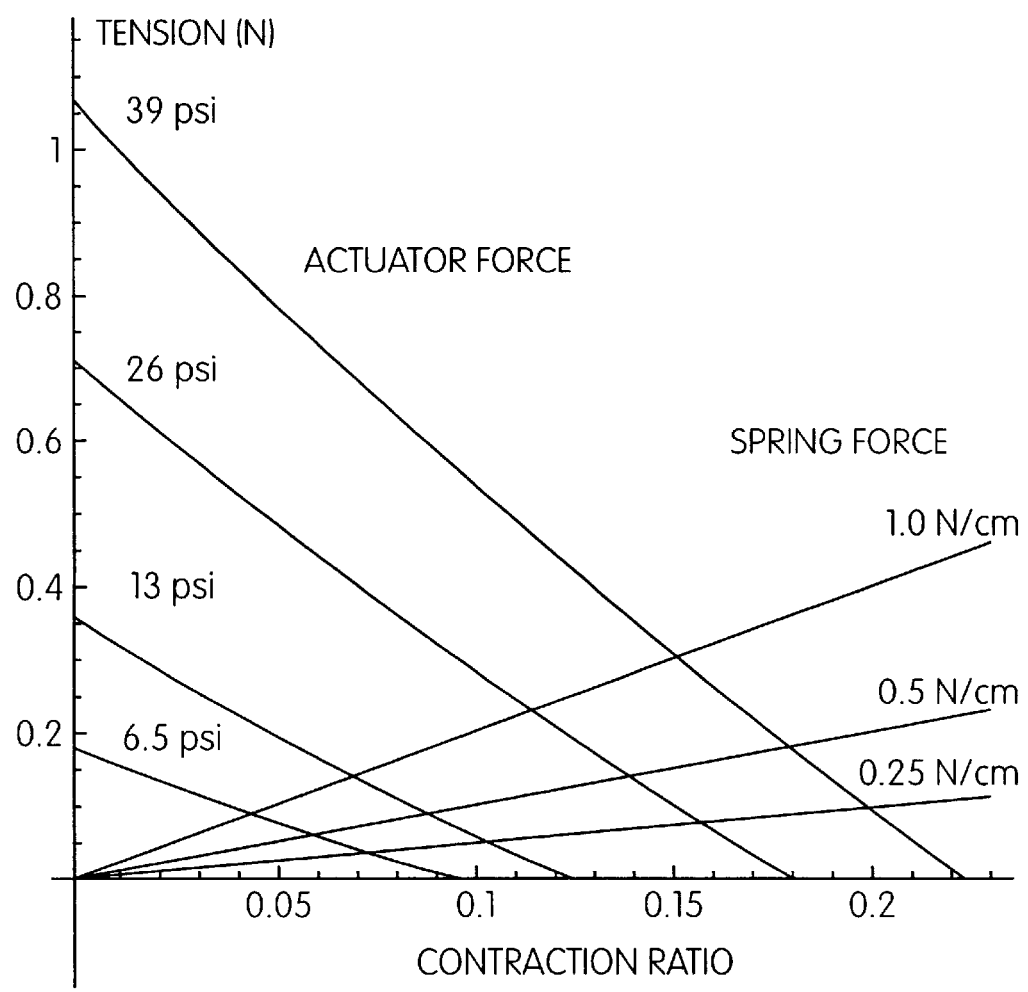
FIG. 14 is a graph of contraction ratio versus tension.

It is possible to determine the static force balance between the internal spring and the McKibben artificial muscle at different pressures using this model. Assuming values of $l_0 = 2.0$ cm, $r_0 = 0.16$ cm, and $\alpha_0 = 30° = \pi/6$, and inflation pressures from 6.5 psi to 39 psi, the predicted static force balance with springs whose stiffnesses range from 0.25 to 1.0 N/cm is shown in FIG. 14. The model makes it possible to predict initial values for the spring constant, which could be modified based on actual measurements.

The speed of peristaltic locomotion can also be modeled using published formulas. In addition to the static force equation, the kinetic frictional forces within the threads of the textile shell of the mesh create a force/velocity property, so that the dynamic force must take into account the velocity dependent frictional forces, the surface of contact over which they operate, and the direction of the velocity. This leads to the following equation for the dynamic model of a McKibben muscle actuator:

$$F_{dynamic} = F_{static} - f S_{contact} P\ \text{sign}(\dot{x}) \quad (6)$$

where $$f = f_k + (f_s - f_k) e^{-\frac{\dot{x}}{x_{ks}}}\ \text{and} \quad (7)$$

$$S_{contact} = (2\pi r_0 l_0) \frac{\sin(\alpha_0)}{(1-\epsilon)\sqrt{1 - \cos(\alpha_0)^2 (1-\epsilon)^2}} \quad (8)$$

and $x = (l_0 - l)$. Constants $f_k$ and $f_s$ are the kinetic and static friction coefficients, respectively. To model the actuator of the invention, the dynamic actuator force (equation 6) is subtracted from the spring force (equation 5), set to zero, and solved for ẋ, the change in length with time.

Using the parameters listed above, setting $f_k=0.015$, $f_s=0.105$, $ẋ_s=0.15$ m/s, and assuming that the pressure is low pass filtered by the capacitance of the tubing with a time constant of 33 ms, yields a graph of change in length over time in response to pulsatile pressure input. As FIGS. 15A–15C indicate, it is likely that each actuator will be able to contract and expand within 100 ms, so that they can be actuated at a rate of 10 Hz.

Figure 15A:
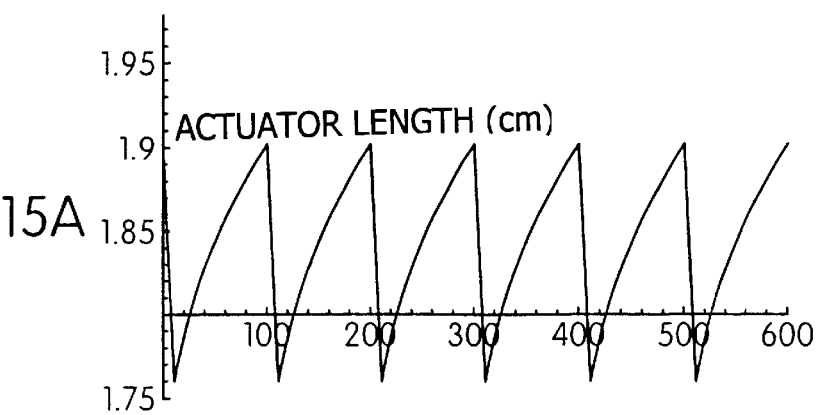
FIGS. 15A–15C are graphs of time versus actuator length, filtered pressure and input pressure, respectively.
Figure 15B:
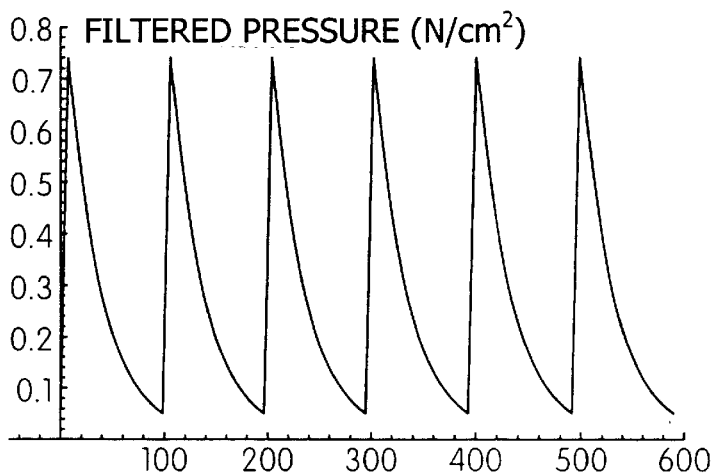
Figure 15C:
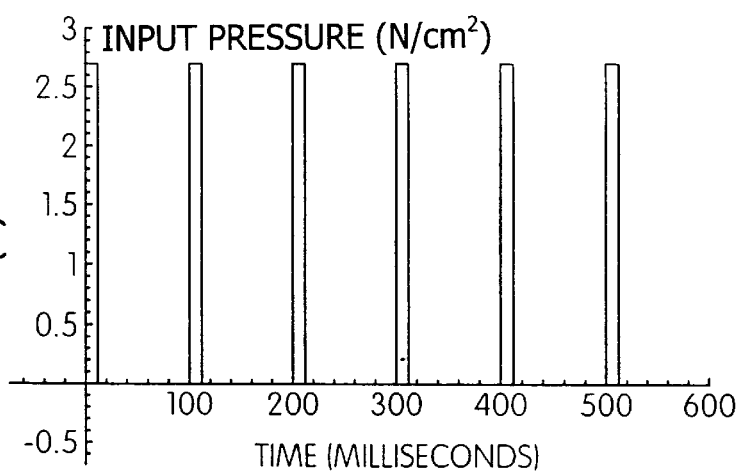

Based on this speed of actuation, the peristaltic motion described in FIGS. 10A–10C, and the kinematics of the invention, it is possible to predict the locomotion speed. As shown in FIG. 15A, each actuator in one example may be assumed to be approximately 1.9 cm in length when deflated, and 1.75 cm in length when inflated, a difference of 0.15 cm. As shown in FIG. 10C, the maximum step size (when the two anterior segments are deflated) is twice this, or 0.3 cm per cycle. Since a single cycle requires that the three actuators be inflated and deflated once, the cycle time is 300 ms. Thus, the locomotion speed is 0.3 cm/300 ms, or 1 cm/s. Preferably, the narrowest portion of the device will always initiate the step, reducing the potential for the device to catch on or damage the anterior part of a biological lumen or vessel. By reversing this sequence, the device can also move backwards.

Figure 16:
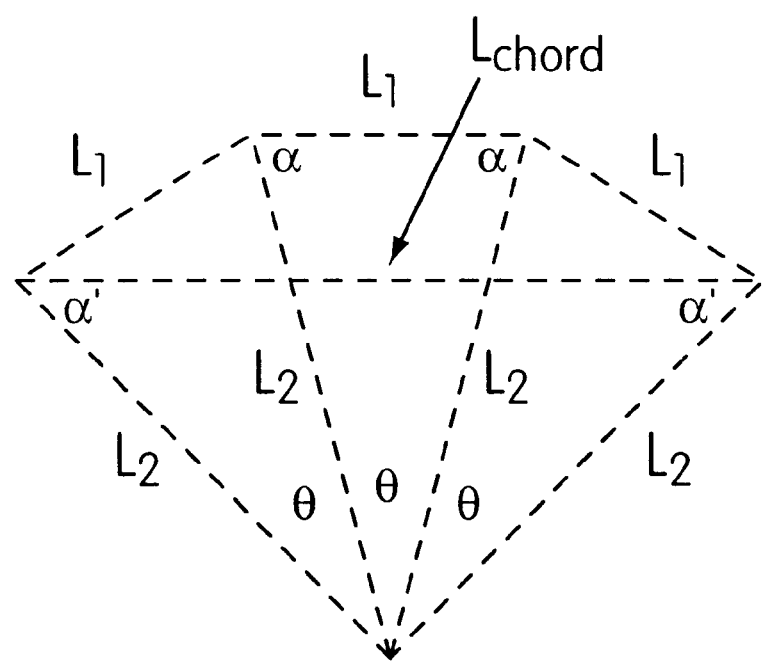
FIG. 16 is a diagram of the geometric components of inchworm movement.

Inchworm locomotion can also be modeled. Referring to FIG. 16, the bases of the bending segments $L_1$ (corresponding to bent actuator length) form the tops of a series of isosceles triangles. By the law of sines, $L_2/\sin \Theta = L_1/\sin \Theta$). Because the triangles are isosceles, $\alpha=\frac{1}{2}(180-\Theta)$, so that $L_2=(L_1/\sin \Theta))\cos(\frac{1}{2}) \alpha$. Similarly, $L_{chord}=\sin n\Theta(L_2/\cos(\frac{1}{2})n\Theta))$, where n is the number of segments. In turn, this implies that $L_{chord}=L_1(\sin n\Theta \cos(\frac{1}{2})\Theta)/(\cos(\frac{1}{2}) n\Theta \sin \Theta))$, which simplifies to $$L_{chord} = L_1 \frac{\sin\frac{1}{2}n\theta}{\sin\frac{1}{2}\theta} \quad (9)$$

The length of the step will be the difference between the relaxed length of each of the segments, $L_{rel}$, times the number of segments n, and the length of the chord $L_{chord}$, or $S=n L_{rel}-L_{chord}$. Assuming that an actuator can bend through an angle of 30°, that an endoscope has 3 segments, that the length $L_1$ of a bent actuator is 1.9 cm, and that the relaxed length $L_{rel}=2.0$ cm, equation (9) predicts that $L_{chord}=5.19$, and thus S=0.8 cm. Assuming a cycle time of about 3 seconds, this would suggest an inchworm locomotion velocity of about 0.8 cm/3 s=0.27 cm/s, about a quarter of the speed for the peristaltic motion. However, even if this mode is somewhat slower, it may sometimes be advantageous to use this motion to move over obstacles.

Although the invention has been described with reference to certain embodiments, the invention is not limited by the embodiments described. The invention includes modifications, variations and equivalents beyond those set forth in the preceding description. By way of example only, the actuator may be caused to expand by means other than fluid pressure. The dimensions and materials given herein are exemplary only, and other dimensions, materials and configurations are within the scope of the invention. The invention is limited only by the attached claims, which claims are to be given the widest scope consistent with the principles disclosed and as may be allowed by the prior art.

What is claimed is:

1. A self-propelled endoscopic device configured for locomotion through a cavity having a substrate contacted by the device, comprising:
   (a) a flexible conduit having a longitudinal dimension along its length, a lateral dimension at any point along the conduit length that is substantially perpendicular to the longitudinal dimension at that point, and an outer wall; and
   (b) a propulsive unit having a maximum laterally-extending gripping surface, the propulsive unit including:
       (i) a first inflatable actuator formed from a first substantially fluid-impermeable bladder, the first bladder:
           having a first end in a fixed longitudinal position on the conduit,
           having a second end opposing the first end, the second end being slidably attached to the conduit and longitudinally movable along the outer wall, and
           being configured to grip the substrate by longitudinally contracting while laterally expanding during propulsion of the device, and
       (ii) a second actuator formed from a second substantially fluid-impermeable bladder, the second bladder:
           having a first end slidably attached to the conduit and longitudinally movable along the outer wall, the first end having at least one point in a substantially fixed position relative to a point on the second end of the first bladder,
           having a second end opposing the first end of the second bladder, the second end being slidably attached to the conduit and longitudinally movable along the outer wall, and
           being configured to grip the substrate by longitudinally contracting while laterally expanding during propulsion of the device, wherein
       the maximum laterally-extending gripping surface is formable by lateral expansion of at least one of the first and second actuators.

2. The self-propelled endoscopic device of claim 1, wherein:
   the first and second bladders comprise respective first and second expansive regions along respective first and second conduit segments, and
   the conduit comprises at least one channel for selectively introducing fluid into and withdrawing fluid from the expansive regions.

3. The self-propelled endoscopic device of claim 2, wherein:
   the first and second bladders comprise respective outer surfaces, at least portions of which form substrate-gripping surfaces,
   the respective outer surfaces are flexible and inextensible, and
   each bladder expands laterally and contracts longitudinally upon introduction of fluid into the respective expansive region of the bladder.

4. The self-propelled endoscopic device of claim 3, wherein:
   the first end of the first bladder is fixedly sealed to the outer wall and a second end of the first bladder is movably sealed to the outer wall, and
   the outer surface of the first bladder surrounds the segment of the outer wall between the first and second ends of the first bladder.

5. The self-propelled endoscopic device of claim 4, wherein:
the first actuator further comprises a restoration spring disposed between the first and second ends of the first bladder, and
the restoration spring biases the first and second ends of the first bladder away from one another when fluid is withdrawn from the first expansive region.

6. The self-propelled endoscopic device of claim 5, wherein at least one actuator further comprises at least one shape memory alloy spring configured to cause bending of that actuator.

7. The self-propelled endoscopic device of claim 4 further comprising a tubular seal comprising a section of flexible fluid-impermeable tubing having two ends, wherein
a first end of the tubular seal is sealed to the outer wall, and
a second end of the tubular seal is sealed to the second end of the first bladder.

8. The self-propelled endoscopic device of claim 2, further comprising a third actuator, the third actuator:
having a first end slidably attached to the conduit and longitudinally movable along the outer wall, the first end having at least one point in a substantially fixed position relative to a point on the second end of the second bladder,
having a second end opposing the first end of the third actuator, the second end being slidably attached to the conduit and longitudinally movable along the outer wall, and
being configured to longitudinally contract while laterally expanding.

9. The self-propelled endoscopic device of claim 2, wherein the endoscope is configured to operate with a gaseous fluid.

10. The self-propelled endoscopic device of claim 2, wherein the endoscope is configured to operate with a liquid fluid.

11. The self-propelled endoscopic device of claim 1, wherein at least one of the bladders comprises at least one external protrusion disposed on a substrate-gripping surface and configured to enhance gripping of the substrate by that bladder.

12. The self-propelled endoscopic device of claim 1, further comprising a thermoplastic bearing joining the first and second actuators and movable longitudinally along the outer wall.

13. The self-propelled endoscopic device of claim 1, further comprising a third actuator, the third actuator:
having a first end slidably attached to the conduit and longitudinally movable along the outer wall, the first end having at least one point in a substantially fixed position relative to a point on the second end of the second bladder,
having a second end opposing the first end of the third actuator, the second end being slidably attached to the conduit and longitudinally movable along the outer wall, and
being configured to longitudinally contract while laterally expanding.

14. The self-propelled endoscopic device of claim 1, further comprising at least one sensor disposed on an outer surface of an actuator and configured to detect changes in a physically measurable quantity.

15. The self-propelled endoscopic device of claim 14, wherein the physically measurable quantity is at least one of light, pressure, temperature, electrical conductivity, electrical resistance or a chemical characteristic.

16. The self-propelled endoscopic device of claim 1, wherein the conduit further comprises at least one channel configured to deliver fluid to a point external to and near a distal end of the endoscopic device.

17. The self-propelled endoscopic device of claim 1, further comprising a control system having a processor configured:
to receive input signals from a user and from a sensor disposed on or near the surface of an actuator, and
to transmit control signals for laterally expanding at least one of the actuators.

18. The self-propelled endoscopic device of claim 17, wherein the processor is configured to issue control signals for peristaltic propulsion.

19. The self-propelled endoscopic device of claim 18, further comprising at least one electrically-operated fluid control valve, wherein the control signals comprise signals causing the valve to allow fluid travel through the conduit so as to permit inflation and deflation of at least one of the bladders.

20. The self-propelled endoscopic device of claim 19, wherein the processor is further configured to transmit control signals for bending at least one of the actuators.

21. The self-propelled endoscopic device of claim 20, wherein the control signals for bending energize a shape memory alloy spring.

22. The self-propelled endoscopic device of claim 21, wherein the processor is configured to selectively modify the propulsive motion and bending of the device based on the signals from the at least one sensor.

23. The self-propelled endoscopic device of claim 19, wherein processor is configured to modify the propulsive motion of the device based on the signals from the at least one sensor.

24. The self-propelled endoscopic device of claim 19, wherein the processor is configured to issue control signals for sequential inflation and deflation of the bladders.

25. The self-propelled endoscopic device of claim 24, wherein the processor is configured to begin inflating one bladder before deflation of an adjacent bladder is complete.

26. The self-propelled endoscopic device of claim 17, wherein the processor is configured to issue the control signals according to an algorithm employing a continuous time recurrent neural network.

27. A self-locomoting machine for probing a confined space, comprising:
a hollow flexible member having a length; and
a propulsive unit having:
a first McKibben actuator surrounding the flexible member, the first actuator having opposed first and second ends, the first end being fixed to the hollow member and the second end movable lengthwise along the hollow member, and
a second McKibben actuator surrounding the flexible member, the second actuator being attached to the first actuator, and having two opposed ends, the two opposed ends of the second actuator being movable lengthwise along the hollow member, wherein
the first actuator is inflatable such that a portion of the first actuator extends farther from the flexible member than remaining portions of the propulsive unit when the second actuator is deflated, and
the second actuator is inflatable such that a portion of the second actuator extends farther from the flexible member than remaining portions of the propulsive unit when the first actuator is deflated.

28. The machine of claim 27, further comprising a third McKibben actuator surrounding the flexible member, attached to the second actuator, and having two opposed ends, the two opposed ends of the third actuator being movable lengthwise along the hollow member.

29. The machine of claim 28, wherein each actuator comprises an internal spring that biases apart the ends of the actuator when internal fluid pressure is reduced.

30. The machine of claim 29, further comprising at least one shape memory alloy spring attached to an internal spring of one of the actuators and configured to bend that actuator upon being energized.

31. The machine of claim 30, further comprising an automated control system configured to control peristaltic motion of the machine.

32. The machine of claim 31, wherein the control system is further configured to control bending motion of the machine.

33. The machine of claim 31, further comprising a sensor located on an exterior surface of one of the actuators.

34. The machine of claim 33, wherein the automated control system is further configured to adjust movement of the machine based upon signals from the sensor.

35. A self-propelled endoscopic device, comprising:
(a) a flexible conduit having a longitudinal dimension along its length, a lateral dimension at any point along the conduit length that is substantially perpendicular to the longitudinal dimension at that point, and an outer wall;
(b) a first inflatable actuator, the first inflatable actuator:
having a first end in a fixed longitudinal position on the conduit,
having a second end opposing the first end, the second end being slidably attached to the conduit and longitudinally movable along the outer wall, and
being configured to longitudinally contract while laterally expanding during propulsion of the device; and
(c) a second actuator, the second actuator:
having a first end slidably attached to the conduit and longitudinally movable along the outer wall, the first end having at least one point in a substantially fixed position relative to a point on the second end of the first actuator,
having a second end opposing the first end of the second actuator, the second end being slidably attached to the conduit and longitudinally movable along the outer wall, and
being configured to longitudinally contract while laterally expanding, wherein:
the first and second actuators comprise respective first and second bladders,
the first and second bladders are each substantially fluid impermeable,
the first and second bladders comprise respective first and second expansive regions along respective first and second conduit segments, and
the conduit comprises at least one channel for selectively introducing fluid into and withdrawing fluid from the expansive regions.

36. The self-propelled endoscopic device of claim 35, wherein:
the first and second bladders comprise respective outer surfaces,
the respective outer surfaces are flexible and inextensible, and
each bladder expands laterally and contracts longitudinally upon introduction of fluid into the respective expansive region of the bladder.

37. The self-propelled endoscopic device of claim 36, wherein:
the first end of the first bladder is fixedly sealed to the outer wall and a second end of the first bladder is movably sealed to the outer wall, and
the outer surface of the first bladder surrounds the segment of the outer wall between the first and second ends of the first bladder.

38. The self-propelled endoscopic device of claim 37, wherein:
the first actuator further comprises a restoration spring disposed between the first and second ends, and
the restoration spring biases the first and second ends of the first actuator away from one another when fluid is withdrawn from the first expansive region.

39. The self-propelled endoscopic device of claim 38, wherein at least one actuator further comprises at least one shape memory alloy spring configured to cause bending of that actuator.

40. The self-propelled endoscopic device of claim 37 further comprising a tubular seal comprising a section of flexible fluid-impermeable tubing having two ends, wherein
a first end of the tubular seal is sealed to the outer wall, and
a second end of the tubular seal is sealed to the second end of the first bladder.

41. The self-propelled endoscopic device of claim 35, further comprising a third actuator, the third actuator:
having a first end slidably attached to the conduit and longitudinally movable along the outer wall, the first end having at least one point in a substantially fixed position relative to a point on the second end of the second actuator,
having a second end opposing the first end of the third actuator, the second end being slidably attached to the conduit and longitudinally movable along the outer wall, and
being configured to longitudinally contract while laterally expanding.

42. The self-propelled endoscopic device of claim 35, wherein the endoscope is configured to operate with a gaseous fluid.

43. The self-propelled endoscopic device of claim 35, wherein the endoscope is configured to operate with a liquid fluid.

44. A self-propelled endoscopic device, comprising:
(a) a flexible conduit having a longitudinal dimension along its length, a lateral dimension at any point along the conduit length that is substantially perpendicular to the longitudinal dimension at that point, and an outer wall;
(b) a first inflatable actuator, the first inflatable actuator:
having a first end in a fixed longitudinal position on the conduit,
having a second end opposing the first end, the second end being slidably attached to the conduit and longitudinally movable along the outer wall, and
being configured to longitudinally contract while laterally expanding during propulsion of the device;
(c) a second actuator, the second actuator:
having a first end slidably attached to the conduit and longitudinally movable along the outer wall, the first end having at least one point in a substantially fixed position relative to a point on the second end of the first actuator, having a second end opposing the first end of the second actuator, the second end being slidably attached to the conduit and longitudinally movable along the outer wall, and being configured to longitudinally contract while laterally expanding; and (d) at least one sensor disposed on an outer surface of an actuator and configured to detect changes in a physically measurable quantity.

45. The self-propelled endoscopic device of claim 44, wherein the physically measurable quantity is at least one of light, pressure, temperature, electrical conductivity, electrical resistance or a chemical characteristic.

46. A self-propelled endoscopic device, comprising:

(a) a flexible conduit having a longitudinal dimension along its length, a lateral dimension at any point along the conduit length that is substantially perpendicular to the longitudinal dimension at that point, and an outer wall;

(b) a first inflatable actuator, the first inflatable actuator:
having a first end in a fixed longitudinal position on the conduit,
having a second end opposing the first end, the second end being slidably attached to the conduit and longitudinally movable along the outer wall, and
being configured to longitudinally contract while laterally expanding during propulsion of the device;

(c) a second actuator, the second actuator:
having a first end slidably attached to the conduit and longitudinally movable along the outer wall, the first end having at least one point in a substantially fixed position relative to a point on the second end of the first actuator,
having a second end opposing the first end of the second actuator, the second end being slidably attached to the conduit and longitudinally movable along the outer wall, and
being configured to longitudinally contract while laterally expanding; and (d) a control system having a processor configured:
to receive input signals from a user and from a sensor disposed on or near the surface of an actuator, and
to transmit control signals for laterally expanding at least one of the actuators.

47. The self-propelled endoscopic device of claim 46, wherein the processor is configured to issue control signals for peristaltic propulsion.

48. The self-propelled endoscopic device of claim 47, further comprising at least one electrically-operated fluid control valve, wherein the control signals comprise signals causing the valve to allow fluid travel through the conduit so as to permit inflation and deflation of at least one of the actuators.

49. The self-propelled endoscopic device of claim 48, wherein the processor is further configured to transmit control signals for bending at least one of the actuators.

50. The self-propelled endoscopic device of claim 49, wherein the control signals for bending energize a shape memory alloy spring.

51. The self-propelled endoscopic device of claim 50, wherein the processor is configured to selectively modify the propulsive motion and bending of the device based on the signals from the at least one sensor.

52. The self-propelled endoscopic device of claim 48, wherein processor is configured to modify the propulsive motion of the device based on the signals from the at least one sensor.

53. The self-propelled endoscopic device of claim 48, wherein the processor is configured to issue control signals for sequential inflation and deflation of the actuators.

54. The self-propelled endoscopic device of claim 53, wherein the processor is configured to begin inflating one actuator before deflation of an adjacent actuator is complete.

55. The self-propelled endoscopic device of claim 46, wherein the processor is configured to issue the control signals according to an algorithm employing a continuous time recurrent neural network.

56. A self-locomoting machine for probing a confined space, comprising:
a hollow flexible member having a length;
a first McKibben actuator surrounding the flexible member and having opposed first and second ends, the first end being fixed to the hollow member and the second end movable lengthwise along the hollow member, the first actuator having an internal spring that biases apart the ends of the actuator when internal fluid pressure is reduced;
a second McKibben actuator surrounding the flexible member, attached to the first actuator, and having two opposed ends, the two opposed ends of the second actuator being movable lengthwise along the hollow member, the second actuator having an internal spring that biases apart the ends of the actuator when internal fluid pressure is reduced;
a third McKibben actuator surrounding the flexible member, attached to the second actuator, and having two opposed ends, the two opposed ends of the third actuator being movable lengthwise along the hollow member, the third actuator having an internal spring that biases apart the ends of the actuator when internal fluid pressure is reduced; and
at least one shape memory alloy spring attached to an internal spring of one of the actuators and configured to bend that actuator upon being energized.

57. The machine of claim 56, further comprising an automated control system configured to control peristaltic motion of the machine.

58. The machine of claim 57, wherein the control system is further configured to control bending motion of the machine.

59. The machine of claim 57, further comprising a sensor located on an exterior surface of one of the actuators.

60. The machine of claim 59, wherein the automated control system is further configured to adjust movement of the machine based upon signals from the sensor.

* * * * *

UNITED STATES PATENT AND TRADEMARK OFFICE
CERTIFICATE OF CORRECTION

PATENT NO. : 6,764,441 B2
DATED : July 20, 2004
INVENTOR(S) : Hillel J. Chiel et al.

It is certified that error appears in the above-identified patent and that said Letters Patent is hereby corrected as shown below:

<u>Title page,</u>
Item [75], Inventor, "Elizabeth D. Mangan" should be replaced with -- Elizabeth V. Mangan --.

Signed and Sealed this

Seventh Day of June, 2005

JON W. DUDAS
*Director of the United States Patent and Trademark Office*